United States Patent

Adhikary

[11] 4,255,573
[45] Mar. 10, 1981

[54] IMIDAZOINDOLE DERIVATIVES AND PHARMACEUTICAL COMPOSITIONS COMPRISING IMIDAZOINDOLE DERIVATIVES

[76] Inventor: Parimal K. Adhikary, 6606 Wilhugh Pl., Nashville, Tenn. 37209

[21] Appl. No.: 25,076

[22] Filed: Mar. 29, 1979

[51] Int. Cl.³ .................. A61K 31/505; C07D 487/14
[52] U.S. Cl. .................... 544/247; 424/251; 544/281; 544/330; 546/304; 546/64; 546/121
[58] Field of Search .......................... 544/247

[56] References Cited

U.S. PATENT DOCUMENTS 2,556,574  6/1951  Cambell et al. .............. 544/247
3,108,108  10/1963  Schellhammer et al. ........ 544/247

Primary Examiner—Donald G. Daus
Assistant Examiner—James H. Turnipseed
Attorney, Agent, or Firm—Quaintance, Murphy & Richardson

[57] ABSTRACT

Pharmaceutical composition for chelating excess iron in a mammal and facilitating the removal of excess iron from the mammalian body are disclosed which comprise as active ingredient an iron-chelating agent selected from the group consisting of 5H-pyrimido(2',1':2,3)imidazo(4,5-b)indole having the formula

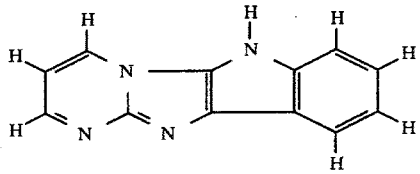

5H-pyrido(2',1':2,3)imidazo(4,5-b) indole having the formula

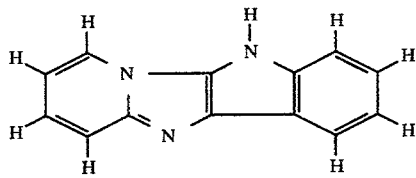

or lower alkyl and/or halogen substituted derivatives thereof and pharmaceutically acceptable acid addition salts thereof. Furthermore the preparation of novel 5H-pyrimido(2',1':2,3)imidazo(4,5-b)indoles and intermediates thereof are disclosed.

2 Claims, No Drawings

IMIDAZOINDOLE DERIVATIVES AND PHARMACEUTICAL COMPOSITIONS COMPRISING IMIDAZOINDOLE DERIVATIVES

CROSS REFERENCE TO RELATED PATENT

In U.S. Pat. No. 4,143,142, 5H-pyrido(2',1':2,3)imidazo(4,5-b)indoles and antihypertensive pharmaceutical compositions containing same are described and claimed.

BACKGROUND OF THE INVENTION

1. Field of the Invention

The invention concerns preparation of novel pyrimidazoindole derivatives and pharmaceutically acceptable acid addition salts thereof; and pharmaceutical compositions for treating excess iron in mammals comprising as an active ingredient a pyrimidoimidazoindole derivative or a pyridoimidazoindole derivative.

2. Description of the Prior Art

The compound 1,2,3,5-tetrahydroimidazo(2,1-b)quinazoline and some of its derivatives with three-ring systems have structural similarity to our compounds with four ring systems and have been reported by Loev, et al., *Journal of Medicinal Chemistry*, 15, 727 (1972) and Jen, et al., *Journal of Medicinal Chemistry*, 15, 727 (1972) as effective antihypertensive agents in animals. However, insofar as is presently known, no one has prepared applicant's imidazoindole derivatives.

SUMMARY OF THE INVENTION

According to this invention there are provided novel 5H-pyrimido(2',1':2,3)imidazo(4,5-b)indole derivatives having the formula I

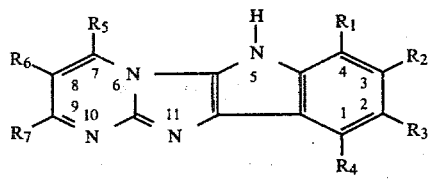

and pharmaceutically acceptable acid addition salts thereof wherein $R_1$, $R_2$, $R_3$ and $R_4$ each are selected from the group consisting of hydrogen, halogen and alkyl containing one to four carbon atoms, with the proviso that when taken together they constitute the following substituents on the tetracyclic ring, 1-halo, 2-halo, 3-halo, 4-halo, 1-alkyl, 2-alkyl, 3-alkyl, 4-alkyl, 1,3-dihalo, 2,3-dihalo, 2,4-dihalo, 3,4-dihalo, 1,3-di-alkyl, 2,3-di-alkyl, 1,4-di-alkyl; $R_5$ is selected from the group consisting of hydrogen and alkyl containing one to four carbon atoms, and $R_6$ and $R_7$ are each selected from the group consisting of hydrogen and halo. Preferably $R_5$, $R_6$, and $R_7$ of formula I are hydrogen.

Furthermore according to the present invention there are provided pharmaceutical compositions for chelating excess iron in a mammal and facilitating the removal of excess iron from the mammalian body which comprise an effective amount of an iron-chelating agent selected from the group consisting of 5H-pyrimido(2',1':2,3)imidazo(4,5-b)indole derivative having the formula I

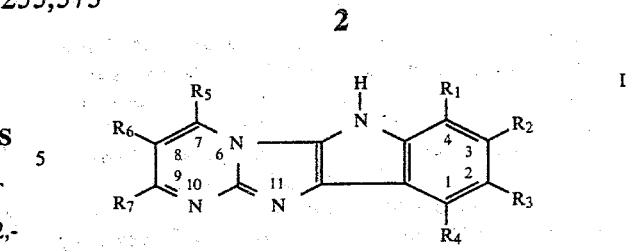

and pharmaceutically acceptable acid addition salts thereof wherein $R_1$, $R_2$, $R_3$ and $R_4$ each are selected from the group consisting of hydrogen, halogen and alkyl containing one to four carbon atoms, with the proviso that when taken together they constitute the following substituents on the tetracyclic ring, 1,-halo, 2-halo, 3-halo, 4-halo, 1-alkyl, 2-alkyl, 3-alkyl, 4-alkyl, 1,3-dihalo, 2,3-dihalo, 2,4-dihalo, 3,4-dihalo, 1,3-di-alkyl, 2,3-di-alkyl, 1,4-di-alkyl; $R_5$ is selected from the group consisting of hydrogen and alkyl containing one to four carbon atoms, and $R_6$ and $R_7$ are each selected from the group consisting of hydrogen and halo; 5-pyrido(2',1':2,3)imidazo(4,5-b)indole derivatives having the formula II

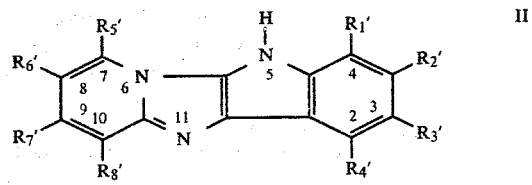

and pharmaceutically acceptable acid addition salts thereof wherein $R_5'$, $R_6'$, $R_7'$, and $R_8'$ each are selected from the group consisting of hydrogen, halogen and alkyl containing one to four carbon atoms, with the proviso that taken together they constitute the following substituents on the tetracyclic ring, 10-halo, 8,10-dihalo, 8,9-di-alkyl and 7,9-di-alkyl; $R_1'$, $R_2'$, $R_3'$ and $R_4'$ are selected from the group consisting of hydrogen, halogen and alkyl containing one to four carbon atoms, with the proviso that when taken together they constitute the following substituents on the tetracyclc ring, 1-halo, 2-halo, 3-halo, 4-halo, 1-alkyl, 2-alkyl, 3-alkyl, 4-alkyl, 1,3-dihalo, 2,3-dihalo, 2,4-dihalo, 3,4-dihalo, 1,3-di-alkyl, 2,3-di-alkyl, 1,4-di-alkyl; and mixtures thereof in association with a pharmaceutical carrier.

Furthermore according to the present invention there are provided methods for chelating excess iron in mammals, for example humans and valuable warm-blooded animals such as laboratory rats, dogs, cats and other domestic animals, and facilitating the removal of excess iron from the mammalian body which comprises administering to a mammal suffering from an excess amount of iron in its body an effective amount of the above described iron-chelating agents, e.g., in form the aforesaid pharmaceutical compositions.

Further objects, features and advantages of the present invention will become apparent from the detailed description of the invention and its preferred embodiments which follows.

DETAILED DESCRIPTION OF THE INVENTION

Most of the compounds of formula I and II are prepared by the phosphite reduction of the corresponding nitroso compounds. The reduction of a nitroso compound by triethylphosphite is described by J. I. Cadogan, *Synthesis*, 1, 11 (1972). The nitroso intermediates of pyridine and pyrimidine are prepared by condensation of an ω-haloacetophenone respectively with 2-aminopyridine and 2-aminopyrimidine as described by Almirante et al., *Journal of Medicinal Chemistry*, 8, 305 (1968) and Almirante et al., *Journal of Medicinal Chemistry*, 9, 29 (1966) and then nitrosation of the resulting base with sodium nitrite and acetic acid as described by LaRocca et al., *Journal of Pharmaceutical Sciences*, 60, 74 (1971).

The preferred method of recovering the imidazoindoles from the phosphite reduction mixture is to let the mixture solidify (about 24 hours required), wash with carbon tetrachloride on a glass filter and recrystallize the residue from 2-propanol or carbon tetrachloride.

The imidazoindoles may also be recovered from the phosphite reduction mixture by allowing it to solidify, washing the solid on a glass filter with cold carbon tetrachloride, taking the residue in a small quantity of chloroform, and eluating it over a column of activated alumina (80–325 mash). The first colored zone is collected, evaporated to dryness and then recrystallized once from 2-propanol.

For the synthesis of most of imidazoindole derivatives of my invention, known phenacyl halides or their ring substituted derivatives are used for condensation respectively with 2-aminopyridines or 2-aminopyrimidine. In those isolated cases where a phenacyl halide with a desired halogen substitution in the ring is not readily available, the desired substitution in the phenyl ring is accomplished by first synthesizing the respective tetracyclic compound without the phenyl ring substituent and later introducing the desired substituent by halogenation. For example: meta-halo-phenacyl halides are not readily available. Therefore the synthesis of 4-halo-5H-pyrido(2′,1′:2,3)imidazo(4,5-b) indole is achieved by subsequent halogenation of the respective unsubstituted tetracyclic imidazoindole derivative.

The condensation reaction and subsequent phosphite reductions may be represented schematically by the following reaction schemes wherein $R_1$, $R_2$, $R_3$, $R_4$, $R_5$, $R_6$, $R_7$, $R_1'$, $R_2'$, $R_3'$, $R_4'$, $R_4'$, $R_5'$, $R_6'$, $R_7'$ and $R_8'$ are as defined above.

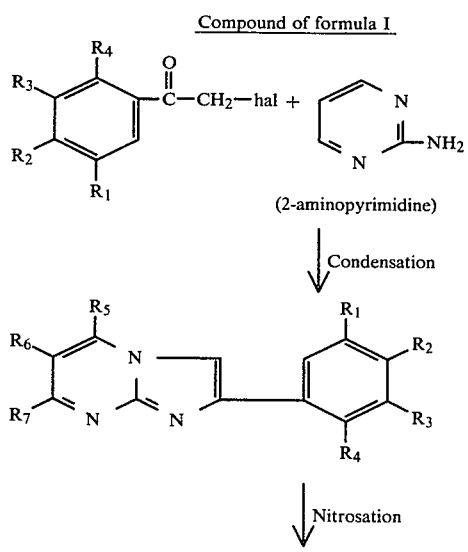

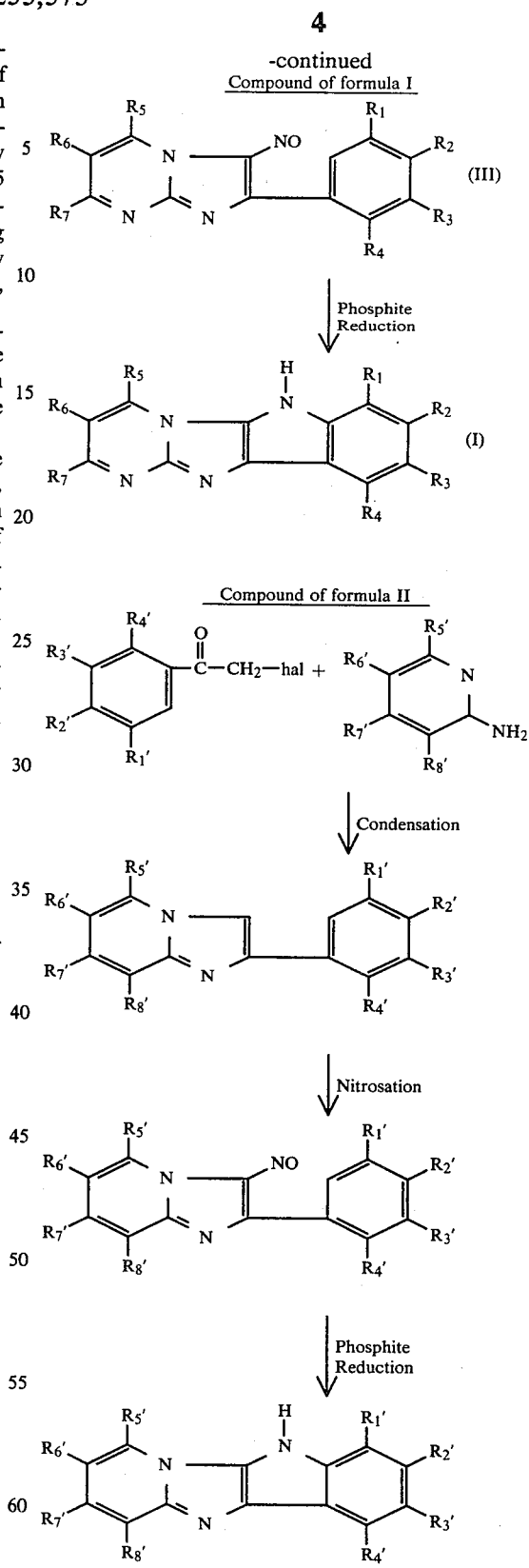

In the foregoing definitions of the substituents, alkyl means methyl, ethyl, propyl, isopropyl, butyl, and the isomeric forms thereof. Halo means chloro, bromo, iodio and fluoro. In the case of a pyridine derivative, the phosphite reduction is complete with 15–30 minutes of refluxing. Further heating yields gradual decomposition of this derivative.

Pharmaceutically acceptable acid addition salts of the compounds of formula I are prepared by reacting a free base of formula I with a stoichiometric amount of an acid, such as hydrogen chloride, hyrogen bromide, hydrogen iodide, sulfuric acid, phosphoric acid, acetic acid, lactic acid, citric acid, succinic acid, benzoic acid, salicylic acid, pamoic acid, cyclohexanesulfamic acid, and the like.

This invention relates also to the pharmaceutical compositions, e.g., in dosage unit forms, for systemic administration (oral and parenteral administration) for treating body iron overload in mammals including humans. The term "dosage unit form" as used in this specification and in the claims refers to physically discrete units suitable as unitary dosages for mammalian subjects, each unit containing a pre-determined quantity of the essential active ingredient, i.e., a compound of formula I or a compound of formula II or a pharmaceutically acceptable acid addition salt thereof, calculated to produce the desired effect in combination with the required pharmaceutical means which adapt the said ingredient for systemic administration. Examples of dosage unit forms in accordance with this invention are tablets, capsules, orally administered liquid preparations in liquid vehicles, sterile preparations in liquid vehicles for intramuscular and intravenous administration, suppositories, and sterile dry preparations for the extemporaneous preparation of sterile injectable preparations in a liquid vehicle. Solid diluents or carriers for the solid oral pharmaceutical dosage unit forms are selected from the group consisting of lipids, carbohydrates, proteins, and mineral solids, for example, starch, sucrose, kaolin, dicalcium phosphate, gelatin, aracia, corn syrup, corn starch, talc and the like. Capsules, both hard and soft, are formulated with conventional diluents and excipients, for example, edible oils, talc, calcium carbonate, calcium stearate and the like. Liquid preparations for oral administration are prepared in water or aqueous vehicles whicadvantageously contain suspending agents, such as for example, ethanol, sodium carboxymethylcellulose, aracia, polyvinyl pyrrolidone, polyvinyl alcohol and the like. In the instance of injectable forms, they must be sterile and must be fluid to the extent that easy syringeability exists. Such preparations must be stable under the conditions of manufacture and storage, and ordinarily contain in addition to the basic solvent or suspending liquid, preservatives in the nature of bactericidal and fungicidal agents, for example, parabens, chlorobutanol, benzyl, alcohol, phenol, thimerosal, and the like. In many cases it is preferable to include isotonic agents, for example sugars or sodium chloride. Carriers and vehicles include vegetable oils, ethanol and polyols, for example, glycerol, propylene glycol, liquid polyethylene glycol and the like. Any solid preparations for subsequent extemporaneous preparation of sterile injectable preparations are sterilized, preferably by exposure to a sterilizing gas, such as for example ethylene oxide. The aforesaid carriers, vehicles, diluents, excipients, preservatives, isotonic agents and the like constitute the pharmaceutical means which adapt the preparations for systemic administration.

The pharmaceutical dosage unit forms are prepared in accordance with the preceeding general description to provide from about 10 mg to about 1 g of the essential active ingredient per dosage unit form.

The compounds of formula I and their pharmaceutically acceptable acid addition salts as well as the compounds of formula II and their pharmaceutically acceptable acid addition salts are capable of binding excess iron in a mammalian body into a chelate-complex as is indicated in standard tests in animals. The adverse physiological effects of such excess iron are substantially reduced and its excretion from the body is largely facilitated.

Due to their capability of chelating body iron the compounds are useful in the treatment of pysiological disorders in mammals in particular humans, which are characterized by an excess amount of iron in the body. Thus the compounds are useful in the treatment of a acute iron intoxication to reduce the toxic effects of the excess iron and facilitate its removal from the body. The compounds are also useful for reducing increased iron-levels in the body in the treatment of chronic iron storage diseases.

In particular the compounds are useful in counteracting transfusional iron overload caused by regular blood transfusions in the treatment of refractory anemia.

For the above mentioned uses the administered doses can vary considerably depending on the type of the compound, the mammal, the mode of administration, the condition which is to be treated and the therapy which is desired. Usually satisfactory body iron reducing effects are obtained with dosages in the range of between about 1 and about 50 mg/kg body weight. These doses can be administered internally, preferably orally, or parenterally. For example, daily oral doses for larger mammals can be chosen between about 100 mg and 500 mg. It is a special advantage of the body-iron chelating compounds of formula I and II that they are expected to be effective upon oral administration.

Among the compounds of formula I and their pharmaceutically acceptable acid addition salts, the compounds wherein $R_1$, $R_2$, $R_3$, $R_4$, $R_5$, $R_6$ and $R_7$ each are hydrogen, that is 5H-pyrimido(2',1':2,3)imidazo(4,5-b)indole or a pharmaceutically acceptable acid addition salt thereof, are preferred.

Among the compounds of formula II and their pharmaceutically acceptable acid addition salts, the compounds wherein $R_1$, $R_2$, $R_3$, $R_4$, $R_5$, $R_6$ and $R_7$ each are hydrogen, that is 5H-pyrido(2',1':2,3)imidazo(4,5-b)indole or a pharmaceutically acceptable acid addition salt thereof, are preferred.

Furthermore the following compounds of formula I and their acid addition salts are suitable for use as body-iron chelating agents according to the present invention:
3-methyl-5H-pyrimido(2',1':2,3)imidazo(4,5-b)indole
3-chloro-5H-pyrimido(2',1':2,3)imidazo(4,5-b)indole
1,3-dichloro-5H-pyrimido(2',1':2,3)imidazo(4,5-b)indole
1,3-dimethyl-5H-pyrimido(2',1':2,3)imidazo(4,5-b)indole
3-bromo-5H-pyrimido(2',1':2,3)imidazo(4,5-b)indole
3-ioda-5H-pyrimido(2',1':2,3)imidazo(4,5-b)indole
3-fluoro-5H-pyrimido(2',1':2,3)imidazo(4,5-b)indole
1,3-dibromo-5H-pyrimido(2',1':2,3)imidazo(4,5-b)indole
1,3-diioda-5H-pyrimido(2',1':2,3)imidazo(4,5-b)indole
1,3-difluoro-5H-pyrimido(2',1':2,3)imidazo(4,5-b)indole
3-ethyl-5H-pyrimido(2',1':2,3)imidazo(4,5-b)indole
3-propyl-5H-pyrimido(2',1':2,3)imidazo(4,5-b)indole
3-isopropyl-5H-pyrimido(2',1':2,3)imidazo(4,5-b)indole
3-n-butyl-5H-pyrimido(2',1':2,3)imidazo(4,5-b)indole 3-sec-butyl-5H-pyrimido(2',1':2,3)imidazo(4,5-b)indole
3-tert-butyl-5H-pyrimido(2',1':2,3)imidazo(4,5-b)indole
4-chloro-5H-pyrimido(2',1':2,3)imidazo(4,5-b)indole
2-chloro-5H pyrimido(2',1':2,3)imidazo(4,5-b)indole
1-chloro-5H-pyrimido(2',1':2,3)imidazo(4,5-b)indole
4-bromo-5H-pyrimido(2',1':2,3)imidazo(4,5-b)indole
2-bromo-5H-pyrimido(2',1':2,3)imidazo(4,5-b)indole
1-bromo-5H-pyrimido(2',1':2,3)imidazo(4,5-b)indole
4-iodo-5H-pyrimido(2',1':2,3)imidazo(4,5-b)indole
2-iodo-5H-pyrimido(2',1':2,3)imidazo(4,5-b)indole
1-iodo-5H-pyrimido(2',1':2,3)imidazo(4,5-b)indole
4-fluoro-5H-pyrimido(2',1':2,3)imidazo(4,5-b)indole
2-fluoro-5H-pyrimido(2',1':2,3)imidazo(4,5-b)indole
1-fluoro-5H-pyrimido(2',1':2,3)imidazo(4,5-b)indole
4-ethyl-5H-pyrimido(2',1':2,3)imidazo(4,5-b)indole
2-ethyl-5H-pyrimido(2',1':2,3)imidazo(4,5-b)indole
1-ethyl-5H-pyrimido(2',1':2,3)imidazo(4,5-b)indole
4-propyl-5H-pyrimido(2',1':2,3)imidazo(4,5-b)indole
2-propyl-5H-pyrimido(2',1':2,3)imidazo(4,5-b)indole
1-propyl-5H-pyrimido(2',1':2,3)imidazo(4,5-b)indole
4-isopropyl-5H-pyrimido(2',1':2,3)imidazo(4,5-b)indole
2-isopropyl-5H-pyrimido(2',1':2,3)imidazo(4,5-b)indole
1-isopropyl-5H-pyrimido(2',1':2,3)imidazo(4,5-b)indole
4-n-butyl-5H-pyrimido(2',1':2,3)imidazo-(4,5-b)indole
2-n-butyl-5H-pyrimido(2',1':2,3)imidazo(4,5-b)indole
1-n-butyl-5H-pyrimido(2',1':2,3)imidazo(4,5-b)indole
4-sec-butyl-5H-pyrimido(2',1':2,3)imidazo(4,5-b)indole
2-sec-butyl-5H-pyrimido(2',1':2,3)imidazo(4,5-b)indole
1-sec-butyl-5H-pyrimido(2',1':2,3)imidazo(4,5-b)indole
4-tert-butyl-5H-pyrimido(2',1':2,3)imidazo(4,5-b)indole
2-tert-butyl-5H-pyrimido(2',1':2,3)imidazo(4,5-b)indole
1-tert-butyl-5H-pyrimido(2',1':2,3)imidazo(4,5-b)indole
2,4-dimethyl-5H-pyrimido(2',1':2,3)imidazo(4,5-b)indole
2,3-dimethyl-5H-pyrimido(2',1':2,3)imidazo(4,5-b)indole
1,2-dimethyl-5H-pyrimido(2',1':2,3)imidazo(4,5-b)indole
1-methyl-5H-pyrimido(2',1':2,3)imidazo(4,5-b)indole
2-methyl-5H-pyrimido(2',1':2,3)imidazo(4,5-b)indole
4-methyl-5H-pyrimido(2',1':2,3)imidazo(4,5-b)indole
2,3-dichloro-5H-pyrimido(2',1':2,3)imidazo(4,5-b)indole
2,4-dichloro-5H-pyrimido(2',1':2,3)imidazo(4,5-b)indole
3,4-dichloro-5H-pyrimido(2',1':2,3)imidazo(4,5-b)indole
2,3-dibromo-5H-pyrimido(2',1':2,3)imidazo(4,5-b)indole
2,4-dibromo-5H-pyrimido(2',1':2,3)imidazo(4,5-b)indole
3,4-dibromo-5H-pyrimido(2',1':2,3)imidazo(4,5-b)indole
b  3,4-dimethyl-5H-pyrimido(2',1':2,3)imidazo(4,5-b)indole Furthermore the following compounds of formula II and their acid addition salts are suitable for use as body-iron chelating agents according to the present invention:

1-methyl-5H-pyrido(2',1':2,3)imidazo(4,5-b)indole
3-chloro-5H-pyrido(2',1':2,3)imidazo(4,5-b)indole
10-methyl-5H-pyrido(2',1':2,3)imidazo(4,5-b)indole
8-chloro-5H-pyrido(2',1':2,3)imidazo(4,5-b)indole
2-methyl-5H-pyrido(2',1':2,3)imidazo(4,5-b)indole
3-methyl-5H-pyrido(2',1':2,3)imidazo(4,5-b)indole
4-methyl-5H-pyrido(2',1':2,3)imidazo(4,5-b)indole
7-methyl-5H-pyride(2',1':2,3)imidazo(4,5-b)indole
8-methyl-5H-pyrido(2',1':2,3)imidazo(4,5-b)indole
9-methyl-5H-pyrido(2',1':2,3)imidazo(4,5-b)indole
10-methyl-5H-pyrido(2',1':2,3)imidazo(4,5-b)indole
1-ethyl-5H-pyrido(2',1':2,3)imidazo(4,5-b)indole
2-ethyl-5H-pyrido(2',1':2,3)imidazo(4,5-b)indole
3-ethyl-5H-pyrido(2',1':2,3)imidazo(4,5-b)indole
4-ethyl-5H-pyrido(2',1':2,3)imidazo(4,5-b)indole
7-ethyl-5H-pyrido(2',1':2,3)imidazo(4,5-b)indole
8-ethyl-5H-pyrido(2',1':2,3)imidazo(4,5-b)indole
9-ethyl-5H-pyrido(2',1':2,3)imidazo(4,5-b)indole
10-ethyl-5H-pyrido(2',1':2,3)imidazo(4,5-b)indole
1-propyl-5H-pyrido(2',1':2,3)imidazo(4,5-b)indole
2-propyl-5H-pyrido(2',1':2,3)imidazo(4,5-b)indole
3-propyl-5H-pyrido(2',1':2,3)imidazo(4,5-b)indole
4-propyl-5H-pyrido(2',1':2,3)imidazo(4,5-b)indole
7-propyl-5H-pyrido(2',1':2,3)imidazo(4,5-b)indole
8-propyl-5H-pyrido(2',1':2,3)imidazo(4,5-b)indole
9-propyl-5H-pyrido(2',1':2,3)imidazo(4,5-b)indole
10-propyl-5H-pyrido(2',1':2,3)imidazo(4,5-b)indole
1-isopropyl-5H-pyrido(2',1':2,3)imidazo(4,5-b)indole
2-isopropyl-5H-pyrido(2',1':2,3)imidazo(4,5-b)indole
3-isopropyl-5H-pyrido(2',1':2,3)imidazo(4,5-b)indole
4-isopropyl-5H-pyrido(2',1':2,3)imidazo(4,5-b)indole
7-isopropyl-5H-pyrido(2',1':2,3)imidazo(4,5-b)indole
8-isopropyl-5H-pyrido(2',1':2,3)imidazo(4,5-b)indole
9-isopropyl-5H-pyrido(2',1':2,3)imidazo(4,5-b)indole
10-isopropyl-5H-pyrido(2',1':2,3)imidazo(4,5-b)indole
1-n-butyl-5H-pyrido(2',1':2,3)imidazo(4,5-b)indole
2-n-butyl-5H-pyrido(2',1':2,3)imidazo94,5-b)indole
3-n-butyl-5H-pyrido(2',1':2,3)imidazo-(4,5-b)indole
4-n-butyl-5H-pyrido(2',1':2,3)imidazo(4,5-b)indole
7-n-butyl-5H-pyrido(2',1':2,3)imidazo(4,5-b)indole
8-n-butyl-5H-pyrido(2',1':2,3)imidazo(4,5-b)indole
9-n-butyl-5H-pyrido(2',1':2,3)imidazo(4,5-b)indole
10-n-butyl-5H-pyrido(2',1':2,3)imidazo(4,5-b)indole
1-sec-butyl-5H-pyrido(2',1':2,3)imidazo(4,5-b)indole
2-sec-butyl-5H-pyrido(2',1':2,3)imidazo(4,5-b)indole
3-sec-butyl-5H-pyrido(2',1':2,3)imidazo(4,5-b)indole
4-sec-butyl-5H-pyrido(2',1':2,3)imidazo(4,5-b)indole
7-sec-butyl-5H-pyrido(2',1':2,3)imidazo(4,5-b)indole
8-sec-butyl-5H-pyrido(2',1':2,3)imidazo(4,5-b)indole
9-sec-butyl-5H-pyrido(2',1':2,3)imidazo(4,5-b)indole
10-sec-butyl-5H-pyrido(2',1':2,3)imidazo(4,5-b)indole
1-tert-butyl-5H-pyrido(2',1':2,3)imidazo(4,5-b)indole
2-tert-butyl-5H-pyrido(2',1':2,3)imidazo(4,5-b)indole
3-tert-butyl-5H-pyrido(2',1':2,3)imidazo(4,5-b)indole
4-tert-butyl-5H-pyrido(2',1':2,3)imidazo(4,5-b)indole
7-tert-butyl-5H-pyrido(2',1':2,3)imidazo(4,5-b)indole
8-tert-butyl-5H-pyrido(2',1':2,3)imidazo(4,5-b)indole
9-tert-butyl-5H-pyrido(2',1':2,3)imidazo(4,5-b)indole
10-tert-butyl-5H-pyrido(2',1':2,3)imidazo(4,5-b)indole
1-chloro-5H-pyrido(2',1':2,3)imidazo(4,5-b)indole
2-chloro-5H-pyrido(2',1':2,3)imidazo(4,5-b)indole
3-chloro-5H-pyrido(2',1':2,3)imidazo(4,5-b)indole
7-chloro-5H-pyrido(2',1':2,3)imidazo(4,5-b)indole
8-chloro-5H-pyrido(2',1':2,3)imidazo(4,5-b)indole
9-chloro-5H-pyrido)2',1':2,3)imidazo(4,5-b)indole
10-chloro-5H-pyrido(2',1':2,3)imidazo(4,5-b)indole
1-bromo-5H-pyrido(2',1':2,3)imidazo(4,5-b)indole
2-bromo-5H-pyrido(2',1':2,3)imidazo(4,5-b)indole
3-bromo-5H-pyrido(2',1':2,3)imidazo(4,5-b)indole
7-bromo-5H-pyrido(2',1':2,3)imidazo(4,5-b)indole
8-bromo-5H-pyrido(2',1':2,3)imidazo(4,5-b)indole
9-bromo-5H-pyrido(2',1':2,3)imidazo(4,5-b)indole
10-bromo-5H-pyrido(2',1':2,3)imidazo(4,5-b)indole
1-fluoro-5H-pyrido(2',1':2,3)imidazo(4,5-b)indole
2-fluoro-5H-pyrido(2',1':2,3)imidazo(4,5-b)indole
3-fluoro-5H-pyrido(2',1':2,3)imidazo(4,5-b)indole 8,9-diisopropyl-5H-pyrido(2',1':2,3)imidazo(4,5-b)indole
1,7-dimethyl-5H-pyrido(2',1':2,3)imidazo(4,5-b)indole
1,8-dimethyl-5H-pyrido(2',1':2,3)imidazo(4,5-b)indole
1,9-dimethyl-5H-pyrido(2',1':2,3)imidazo(4,5-b)indole
1,10-dimethyl-5H-pyrido(2',1':2,3)imidazo(4,5-b)indole
2,7-dimethyl-5H-pyrido(2',1':2,3)imidazo(4,5-b)indole
2,8-dimethyl-5H-pyrido(2',1':2,3)imidazo(4,5-b)indole
2,9-dimethyl-5H-pyrido(2',1':2,3)imidazo(4,5-b)indole
2,10-dimethyl-5H-pyrido(2',1':2,3)imidazo(4,5-b)indole
3,7-dimethyl-5H-pyrido(2',1':2,3)imidazo(4,5-b)indole
3,8-dimethyl-5H-pyrido(2',1':2,3)imidazo(4,5-b)indole
3,9-dimethyl-5H-pyrido(2',1':2,3)imidazo(4,5-b)indole
3,10-dimehtyl-5H-pyrido(2',1':2,3)imidazo(4,5-b)indole
4,7-dimethyl-5H-pyrido(2',1':2,3)imidazo(4,5-b)indole
4,8-dimethyl-5H-pyrido(2',1':2,3)imidazo(4,5-b)indole
4,9-dimethyl-5H-pyrido(2',1':2,3)imidazo(4,5-b)indole
4,10-dimethyl-5H-pyrido(2',1':2,3)imidazo(4,5-b)indole
2,4-dimethyl-5H-pyrido(2',1':2,3)imidazo(4,5-b)indole
10-chloro-4-methyl-5H-pyrido(2',1':2,3)imidazo(4,5-b)indole
10-bromo-4-methyl-5H-pyrido(2',1':2,3)imidazo(4,5-b)indole
10-chloro-4-ethyl-5H-pyrido(2',1':2,3)imidazo(4,5-b)indole
10-chloro-4-butyl-5H-pyrido(2',1':2,3)imidazo(4,5-b)indole
10-chloro-4-propyl-5H-pyrido(2',1':2,3)imidazo(4,5-b)indole
10-chloro-2,4-dimethyl-5H-pyrido(2',1':2,3)imidazo(4,5-b)indole
10-chloro-2,4-diethyl-5H-pyrido(2',1':2,3)imidazo(4,5-b)indole
10-chloro-2,4-dipropyl-5H-pyrido(2',1':2,3)imidazo(4,5-b)indole
7-fluoro-5H-pyrido(2',1':2,3)imidazo(4,5-b)indole
8-fluoro-5H-pyrido(2',1':2,3)imidazo(4,5-b)indole
9-fluoro-5H-pyrido(2',1':2,3)imidazo(4,5-b)indole
10-fluoro-5H-pyrido(2',1':2,3)imidazo(4,5-b)indole
1-iodo-5H-pyrido(2',1':2,3)imidazo(4,5-b)indole
2-iodo-5H-pyrido(2',1':2,3)imidazo(4,5-b)indole
3-iodo-5H-pyrido(2',1':2,3)imidazo(4,5-b)indole
7-iodo-5H-pyrido(2',1':2,3)imidazo(4,5-b)indole
8-iodo-5H-pyrido(2',1':2,3)imidazo(4,5-b)indole
9-iodo-5H-pyrido(2',1':2,3)imidazo(4,5-b)indole
10-iodo-5H-pyrido(2',1':2,3)imidazo(4,5-b)indole
1,3-dichloro-5H-pyrido(2',1':2,3)imidazo(4,5-b)indole
2,3-dichloro-5H-pyrido(2',1':2,3)imidazo(4,5-b)indole
2,4-dichloro-5H-pyrido(2',1':2,3)imidazo(4,5-b)indole
3,4-dichloro-5H-pyrido(2',1':2,3)imidazo(4,5-b)indole
1,3-dibromo-5H-pyrido(2',1':2,3)imidazo(4,5-b)indole
2,3-dibromo-5H-pyrido(2',1':2,3)imidazo(4,5-b)indole
2,4-dibromo-5H-pyrido(2',1':2,3)imidazo(4,5-b)indole
3,4-dibromo-5H-pyrido(2',1':2,3)imidazo(4,5-b)indole
8,10-dibromo-5H-pyrido(2',1':2,3)imidazo(4,5-b)indole
8,10-dichloro-5H-pyrido(2',1':2,3)imidazo(4,5-b)indole
7,9-dimethyl-5H-pyrido(2',1':2,3)imidazo(4,5-b)indole
7,9-diethyl-5H-pyrido(2',1':2,3)imidazo(4,5-b)indole
7,9-dipropyl-5H-pyrido(2',1':2,3)imidazo(4,5-b)indole
7,9-diisopropyl-5H-pyrido(2',1':2,3)imidazo(4,5-b)indole
7,9-di-n-butyl-5H-pyrido(2',1':2,3)imidazo(4,5-b)indole
7,9-dimethyl-5H-pyrido(2',1':2,3)imidazo(4,5-b)indole
8,9-dimethyl-5H-pyrido(2',1':2,3)imidazo(4,5-b)indole
8,9-diethyl-5H-pyrido(2',1':2,3)imidazo(4,5-b)indole
8,9-dipropyl-5H-pyrido(2',1':2,3)imidazo(4,5-b)indole
10-chloro-2,4-dibutyl-5H-pyrido(2',1':2,3)imidazo(4,5-b)indole
4,10-dichloro-5H-pyrido(2',1':2,3)imidazo(4,5-b)indole
4,10-dibromo-5H-pyrido(2',1':2,3)imidazo(4,5-b)indole
10-chloro-2,4-dibromo-5H-pyrido(2',1':2,3)imidazo(4,5-b)indole
10-chloro-2,4-dichloro-5H-pyrido(2',1':2,3)imidazo(4,5-b)indole
10-bromo-2,4-dibromo-5H-pyrido(2',1':2,3)imidazo(4,5-b)indole
10-bromo-2,4-dichloro-5H-pyrido(2',1':2,3)imidazo(4,5-b)indole
4-chloro-9-methyl-5H-pyrido(2',1':2,3)imidazo(4,5-b)indole
2,4-dichloro-9-methyl-5H-pyrido(2',1':2,3)imidazo(4,5-b)indole
2,4-dichloro-9-ethyl-5H-pyrido(2',1':2,3)imidazo(4,5-b)indole
2,4-dichloro-9-propyl-5H-pyrido(2',1':2,3)imidazo(4,5-b)indole
2,4-dichloro-9-butyl-5H-pyrido(2',1':2,3)imidazo(4,5-b)indole
2,4-dibromo-9-methyl-5H-pyrido(2',1':2,3)imidazo(4,5-b)indole
2,4-dibromo-9-ethyl-5H-pyrido(2',1':2,3)imidazo(4,5-b)indole
2,4-dibromo-9propyl-5H-pyrido(2',1':2,3)imidazo(4,5-b)indole
2,4-dibromo-9-butyl-5H-pyrido(2',1':2,3)imidazo(4,5-b)indole The preparation of the above listed 5H-pyrido(2',1':2,3)imidazo(4,5-b)indole derivatives is disclosed in U.S. Pat. No. 4,143,142, the disclosure of which is hereby incorporated by reference.

The following examples describe the manner and process of making and using the invention and set forth the best mode contemplated by the inventor of carrying out the invention but are not to be construed as limiting.

EXAMPLE 1

Preparation of the intermediate compound 3-nitroso-2-phenylimidazo(1,2-a)pyrimidine (A) A mixture of 9.5 g of 2-aminopyrimidine (0.1 mole), 20 g of ω-bromoacetophenone (0.1 mole) and 200 ml of 95% ethanol is refluxed for three hours and then heated at 60° for an additional 12 hours with stirring. After cooling, the reaction product is condensed to a thick liquid by evaporating it in a rotary evaporator. The residue is mixed with 500 ml of methylene chloride and 100 ml of 3 N sodiumhydroxide solution. The mixture is stirred for 10 minutes and then separated in two layers in a separatory funnel. The lower layer (solvent) is collected, washed with 100 ml of water and then evaporated to dryness under reduced pressure. The residue is washed with 2-propanol on a glass filter and dried in vacuum to yield about 20 g of 2-phenylimidazo(1,2-a)pyrimidine, m.p. 200° to 202° C.

(B) A mixture of 20 g of 2-phenylimidazo(1,2-a)pyrimidine, 200 ml of glacial acetic acid and 20 ml of water is warmed with stirring until the solids are completely dissolved. The solution is next cooled to 5° C. in an ice/salt bath. A solution of 15 g of NaNO$_2$ in 50 ml of water is added dropwise to the cooled acetic acid solution while the solution is kept between 0°–5° C. throughout the addition of NaNO$_2$ solution and three hours thereafter. The reaction mixture is further stirred for 12 more hours at room temperature. The green precipitate is filtered and washed thoroughly with water on a glass filter. The residue is recrystallized once from 2-propanol to yield about 15 g of 3-nitroso-2-phenylimidazo(1,2-a)pyrimidine, m.p. 223°–225° C.

EXAMPLE 2

Preparation of pyrimidino(2',1':2,3)imidazo(4,5-b)indole

A mixture of 9.0 g of analytically pure 3-nitroso-2-phenylimidazo(1,2-a)pyrimidine (0.04 mol) and 10 ml of 97% triethylphosphite (0.05 mol) in 50 ml of anhydrous toluene is refluxed for 1 hour with stirring and under a constant flow of dry nitrogen gas. The temperature of the oil bath is kept between 110° and 120° C. After cooling the solvent and excess triethylphosphite are removed by vacuum distillation at 0.2 Torr. The temperature of the oil bath was kept under 120° C. during the distillation. The residue, which is a thick liquid, is kept overnight at 0° C. during which time it solidifies. The solid is washed on a glass filter with cold carbon tetrachloride and then recrystallized from CCl$_4$. Yield about 5 g, m.p. 96° to 98° C.

Analysis calculated for $C_{12}H_8N_4$—found: C:69.34; H:3.95: N:26.79.

EXAMPLE 3

Preparation of 3-methyl-5H-pyrimido(2',1':2,3)imidazo(4,5-b)indole

Utilizing the procedure of Example 2 and substituting 3-nitroso-2-(4-methylphenyl)imidazo(1,2-a)pyrimidine for 3-nitroso-2-phenylimidazo(1,2-a)pyrimidine, the compound 3-methyl-5H-pyrimido(2',1':2,3)imidazo(4,5-b)indole is obtained.

EXAMPLE 4

Preparation of 3-chloro-5H-pyrimido(2',1':2,3)imidazo(4,5-b)indole

Utilizing the procedure of Example 2 and substituting 3-nitroso-2-(4-chlorophenyl)imidazo(1,2-a)pyrimidine for 3-nitroso-2-phenylimidazo(1,2-a)pyrimidine, the compound 3-chloro-5H-pyrimido(2',1':2,3)imidazo(4,5-b)indole is obtained.

EXAMPLE 5

Preparation of 3,1-dichloro-5H-pyrimido(2',1':2,3)imidazo(4,5-b)indole

Utilizing the procedure of Example 2 and substituting 3-nitroso-2-(2,4-dichlorophenyl)imidazo(1,2-a)pyrimidine for 3-nitroso-2-phenylimidazo(1,2-a)pyrimidine, the compound 3,1-dichloro-5H-pyrimido(2',1':2,-3)imidazo(4,5-b)indole is obtained.

EXAMPLE 6

Preparation of 3,1-dimethly-5H-pyrimido(2',1':2,3)imidazo(4,5-b)indole

Utilizing the procedure of Example 2 and substituting 3-nitroso-2-(2,4-dimethylphenyl)imidazo(1,2-a)pyrimidine for 3-nitroso-2-phenylimidazo(1,2-a)pyrimidine, the compound: 3,1-dimethyl-5H-pyrimido(2',1':2,-3)imidazo(4,5-b)indole is obtained.

Further utilizing the procedure of Example 2 and substituting the appropriate nitroso compounds, the derivatives of the pyrimido-imidazo-indoles which are listed on Pages 14 to 16 are prepared.

Starting materials for preparing the nitroso intermediates of the pyrimidine derivatives are commercially available or may be synthesized by methods known in the art.

EXAMPLE 7

Pharmaceutical compositions for the treatment of excess body iron

A. Capsules
Composition per single dosage unit:
5H-pyrimido(2',1':2,3)imidazo(4,5-b)indole 50 mg of analytically pure compound per capsule to be given 1 to 4 times daily.

B. Solution for Injection
Composition per single dosage unit:
5H-pyrimido(2',1':2,3)imidazo(4,5-b)indole hydrochloride 40 mg in sterile water, 2 ml per ampule to be given i.v.; s.c.; or i.p. 1 to 4 times daily.

What is claimed is:

1. A compound selected from the group of 5H-pyrimido(2',1':2,3)imidazo(4,5-b)indole derivatives having the formula

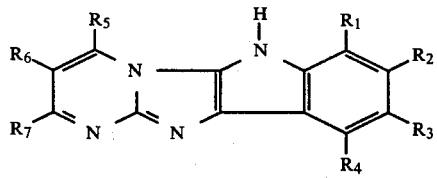

and pharmaceutically acceptable acid solution salts thereof wherein $R_1$, $R_2$, $R_3$, and $R_4$ each are selected from the group consisting of hydrogen, halogen, and alkyl having one to four carbon atoms, with the proviso that when taken together they constitute the following substituents on the tetracyclic ring, 1-halo, 2-halo, 3-halo, 4-halo, 1-alkyl, 2-alkyl, 3-alkyl, 4-alkyl, 1,3-dihalo, 2,3-dihalo, 2,4-dihalo, 3,4-dihalo, 1,3-di-alkyl, 2,3-dialkyl, 1,4-di-alkyl; $R_5$ is selected from the group consisting of hydrogen and alkyl containing one to four carbon atoms, and $R_6$ and $R_7$ each are selected from the group consisting of hydrogen and halo.

2. The compound as defined in claim 1 wherein $R_1$, $R_2$, $R_3$, $R_4$, $R_5$, $R_6$, and $R_7$ each are hydrogen, which is 5H-pyrimido(2',1':2,3)imidazo(4,5-b)indole or a pharmaceutically acceptable acid addition salt thereof.

* * * * *